United States Patent [19]

Robinson et al.

[11] 4,420,978
[45] Dec. 20, 1983

[54] METHOD AND DEVICE FOR TRANSMITTING AND RECEIVING ELECTRO-MAGNETIC ULTRASOUND

[75] Inventors: Thomas Robinson; Willy Ohlsson, both of Nyköping, Sweden

[73] Assignee: Studsvik Energiteknik AB, Nyköping, Sweden

[21] Appl. No.: 251,888

[22] Filed: Apr. 7, 1981

[30] Foreign Application Priority Data

Apr. 18, 1980 [SE] Sweden .............................. 8002948

[51] Int. Cl.³ ........................................... G01N 29/04
[52] U.S. Cl. ....................................... 73/643; 73/602; 328/165
[58] Field of Search ................. 73/627, 643, 668, 602; 367/43, 48, 59; 328/165

[56] References Cited

U.S. PATENT DOCUMENTS

| | | | |
|---|---|---|---|
| 3,638,175 | 1/1972 | Stone | 367/48 |
| 3,786,409 | 1/1974 | Sorkin | 367/59 |
| 4,093,923 | 6/1978 | McCormick | 328/165 |
| 4,314,479 | 2/1982 | Spijkerman | 73/643 |

Primary Examiner—Howard A. Birmiel
Attorney, Agent, or Firm—LeBlanc, Nolan, Shur & Nies

[57] ABSTRACT

A method at the transmission and reception of electro-magnetically generated and received pulses of ultrasound, especially at non-destructive testing of electrically conductive material.

The method comprises the steps of in a transmitter generating a first magnetic field by means of a first coil and a magnet core and supplying a transmitter coil located in the first magnetic field with a transmission pulse of ultrasonic frequency, and in a receiver generating a second magnetic field by means of a second coil and magnet core and by means of a receiver coil located in the second magnetic field receiving a signal originating from said transmitted pulse. When testing in this way nonmagnetic material, the signal/noise ratio is low. The noise partially originates from generated ultrasound affecting the transmitter and receiver magnets.

According to the invention, a first transmission pulse is caused to be transmitted and received while the current in said first coil (1) and said second coil (2) has the same or different direction, whereafter the received signal is stored in a memory (8) intended therefor, whereafter a second transmission pulse is caused to be transmitted and received while the current in said first coil (1) or said second coil (2) has reversed direction compared with the condition when the first transmission pulse was transmitted and received, whereafter the difference between the signal last received and said stored signal is formed.

By the present invention, after said difference has been formed a signal substantially free of interference is received.

The invention further comprises a device for carrying out said method.

5 Claims, 6 Drawing Figures

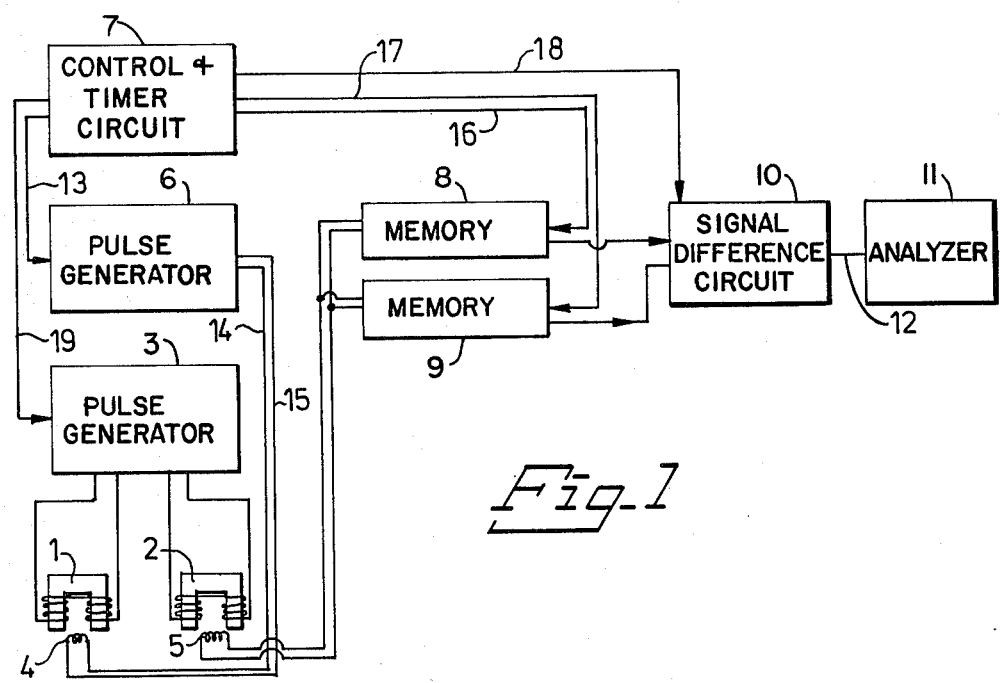
Fig. 1
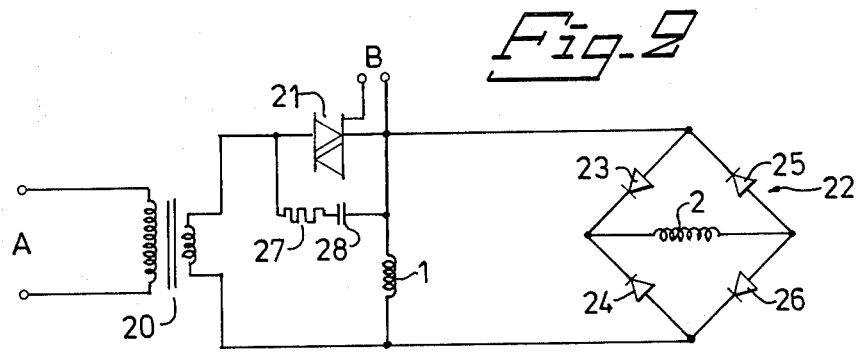
Fig. 2
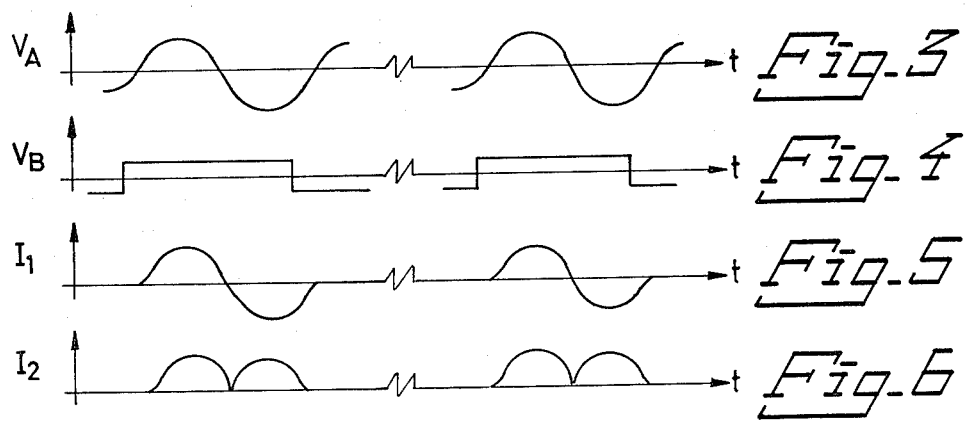
Fig. 3
Fig. 4
Fig. 5
Fig. 6

METHOD AND DEVICE FOR TRANSMITTING AND RECEIVING ELECTRO-MAGNETIC ULTRASOUND

This invention relates to a method and a device for transmitting and receiving electromagnetic ultrasound.

Electromagnetic ultrasonic testing is applied with special advantage when materials are to be tested where the transmitter cannot be arranged in direct contact with the test material. One very essential application is the indication of defects on steel workpieces and on products in heated condition. When the temperature of the test material exceeds the Curie temperature, the signal/noise level of the signal drops substantially, and as a result thereof it is difficult to clearly detect the signal received.

The principle of electromagnetic ultrasonic testing is, that electromagnets are activated, whereafter an ultrasonic pulse, which in most cases is sinusoidal, is transmitted from a generator to a transmitter coil located in the field from the electromagnet of the transmitter. The current in the transmitter coil induces a corresponding varying current into the test material surface. Due to a magnetic field B existing in a conductor and simultaneously a current I flowing in the conductor (i.e. the test material), a force F, the so-called Lorentz force, develops on the conductor, which force is equal to $$F = I \times B$$

where the dimension of I is A/m$^2$ and B Tesla

In this case the force is oscillating with ultrasonic frequency, whereby elastic ultrasonic waves are introduced into the test material.

Upon arrival of the ultrasonic waves at a receiver, according to Faraday's law of induction a corresponding electric signal is generated in a receiver coil, which is located in a magnetic field from the electromagnet of the receiver.

In an ideal system the entire signal received by the receiver originates from ultrasonic waves, which were propagated and reflected in the test material.

Vibrations in the transmitter and receiver magnets, due to generated ultrasonic waves acting thereon, give rise to reception interferences, which in view of the low signal/noise ratio have a considerable level.

In a practical system, therefore, the signal received originates, besides from signals reflected in the material, from interferences, vibrations whereof in the transmitter and receiver magnets are a considerable interference source.

The present invention solves this problem by eliminating the influence of vibrations in the transmitter and receiver magnets.

The invention, thus, implies a substantial improvement in the signal/noise ratio at electromagnetic ultrasonic testing.

The present invention relates to a method at the transmission and reception of electromagnetically generated and received ultrasonic pulses, especially at non-destructive testing of electrically conductive materials, especially steel with a temperature above the Curie temperature, comprising the steps of generating in a transmitter a first magnetic field by means of a first coil and a magnet core, and supplying to a transmitter coil located in the first magnetic field a transmission pulse of ultrasonic frequency, of generating in a receiver a second magnetic field by means of a second coil and a magnet core, and to receive by means of a receiver coil located in the second magnetic field a signal originating from said transmitted pulse, which method is characterized in that a first transmission pulse is caused to be transmitted and received while the current in said first and said second coil have the same or different direction, whereafter the signal received is stored in a memory intended therefor, that thereafter a second transmission pulse is caused to be transmitted and received while the current either in said first coil or in said second coil has a direction reversed compared to the condition when the first transmission pulse was transmitted and received, that the difference between the signal last received and said stored signal is formed, whereafter the difference constitutes a signal received substantially without interference.

The invention also relates to a device of the kind and having the characterizing features as defined in the attached claim 6.

The invention is described in the following with reference to the accompanying drawing, which by way of example shows an embodiment, and in which FIG. 1 is a schematic block diagram of a device, to which the invention is applied, FIG. 2 shows a pulse generator for a transmitter and receiver magnet, FIGS. 3 and 4 are voltage-time diagrams, FIGS. 5 and 6 are current intensity-time diagrams.

In FIG. 1 a device is shown, at which the invention is utilized. A transmitter magnet 1 and a receiver magnet 2, both comprising an iron core with associated winding, are provided spaced from one another. The transmitter and receiver magnets 1,2 are capable to generate a relatively strong magnetic field. The effect in said magnets 1,2 is generated by a first pulse generator 3, which is capable at transmission and reception to supply the windings in the magnets 1,2 with current.

In immediate connection to the poles of the transmitter and, respectively, receiver magnet a transmitter coil 4 and, respectively, a receiver coil 5 are located. A second pulse generator 6 is provided to transmit a short pulse of preferably well-defined length through the transmitter coil 4 while the magnetic field of the transmitter magnet 1 is strong, preferably below its maximum strength.

The ultrasonic pulse thus generated in an electrically conductive test material is reflected in the test material and received by the receiver coil 5, which receives the generated ultrasonic pulse while the magnetic field of the receiver magnet 2 is strong, in a manner corresponding to that mentioned above for the transmitter magnet.

A control and time circuit 7 is capable to transmit an impulse to the first pulse generator 3 via a conductor 19 to transmit a current pulse through the transmitter and receiver magnets, and is capable, when the magnetic fields from said magnets are strong, to transmit an impulse to the second pulse generator 6 to transmit a pulse of ultrasonic frequency through the transmitter coil 4.

The aforesaid components, viz. the time circuit 7 as well as the first and the second pulse generator 3 and, respectively, 6 can be of a suitable known type.

The functional principle for receiving the transmitted ultrasound is such, that ultrasound reflected in the test material and the applied magnetic field from the receiver magnet 2 give rise to an electromotive force (emf) (e) in the receiver coil, i.e. a signal which can be amplified and presented.

The present invention is based on the understanding, that the consequence of a current reversal, for example in the coil of the transmitter magnet 1, is not the same for the emf proportion of the receiver signal, which is corresponded by real ultrasonic waves after propagation through the test material, as for the proportions ($e_1$), which is corresponded by vibrations in the transmitter and receiver magnets.

When the original polarity of the transmitter magnet is called p, the receiver signal can be expressed as $$e_p = e_{op} + e_{1p} \quad (1)$$

When the polarity of the transmitter magnet is reversed and called m, the receiver signal can be expressed as $$e_m = e_{om} + e_{1m} \quad (2)$$

but $$e_{op} = -e_{om} = e_o \quad (3)$$

because the ultrasound generating forces in the sample are reversed.

The ultrasonic vibrations in the transmitter magnet are reversed at the reversing of the current in the winding of the transmitter magnet. If only this should apply, then $e_{1p} = -e_{1m}$, but it has to be taken into account that also the polarity of the transmitter magnet is reversed. This implies a double reversing for the emf in the receiver coil originating from interferences. Thus $$e_{1m} = e_{1p} \quad (4)$$

By carrying out two subsequent ultrasound observations with different transmitter magnet polarities, and then taking the difference between the two corresponding receiver signals, one obtains $$e_p - e_m = e_{op} + e_{1p} - e_{om} - e_{1m} \quad (5)$$

With the equation (3) and (4) one obtains $$e_p - e_m = 2 e_o \quad (6)$$

Thus, receiver signals originating from magnet vibrations have disappeared in the difference, which as a result only yields a double signal corresponding to the real ultrasonic waves, which have been propagated in the test material.

Instead of taking the difference between two signals received at different directions in the winding of the transmitter magnet, the same result is obtained when in a similar way the difference is taken for two different current directions in the winding of the receiver magnet.

In the foregoing the relation with respect to interferences originating from transmitter-receiver vibrations has been dealt with. The same argumentation shows that the difference between two signals received at different current directions in the winding of the transmitter magnet also yields the elimination of influences from vibrations in the receiver magnet. As an alternative procedure yielding the same favourable result it also is possible merely to reverse the polarity of the receiver magnet.

In other words, the difference between the two signals yields a signal entirely free from interferences caused by vibrations both in the transmitter and receiver electromagnet. A further advantage of this method is, that the unavoidable noise (of thermodynamic origin), which is characteristic of all sufficienly sensitive measuring systems, is relative to the desired ultrasonic signal strength reduced by the procedure proper of taking the difference.

The signal/noise ratio is improved by the invention by a factor of about 1.4.

For the above purpose, viz. taking the difference of two subsequent signals received, two memories 8,9 of known type are provided. A difference circuit 10 of known type also is provided to form the difference of the two signals stored in the respective memories 8,9. An analizer and/or visual instrument 11 is connected to the output 12 of the difference circuit 10.

The aforesaid time circuit 7 is capable, after it has transmitted a signal to the second pulse generator 6 through the conductor 13, whereby the pulse generator transmits a transmitter pulse to the coil 4 via the conductors 14,15, to transmit a signal to the first memory 8 via a conductor 16 to store the signal received in the receiver coil 5, which signal originates from the transmitted transmission pulse of ultrasonic frequency. The time circuit 7 further is capable, after it has transmitted a subsequent pulse to the second pulse generator 6 through the conductor 13, whereby the pulse generator transmits a second transmission pulse to the coil 4, to transmit a signal to the second memory 9 via a conductor 17 to store the signal received in the receiver coil 5, which signal originates from the second transmitted transmission pulse.

The time circuit 7 is capable thereafter to transmit a signal via a conductor 18 to the difference circuit 10 to form the difference between the signal stored in the first memory and, respectively, second memory 9.

In FIG. 2 a preferred embodiment of the first pulse generator 3 is shown in greater detail.

The input B in FIG. 2 is the same as the input of the conductor 19 in the first pulse generator 3. The input A is connected to mains voltage with a frequency of 50 cps.

A transformer 20 is located between the input A and the remainder of the circuit in the pulse generator 3. The pulse generator 3 comprises a double thyristor 21 and a rectifier bridge 22 with four diodes 23–26. An attenuation circuit is provided which comprises a resistor 27 and a condenser 28 in series and connected in parallel over the double thyristor 21.

The circuit in FIG. 2 has the function as follows. It is described with reference to FIGS. 3,4,5 and 6, of which FIG. 3 shows the voltage over A, FIG. 4 shows the voltage over B, FIG. 5 shows the current intensity through the coil 1, and FIG. 6 shows the current intensity through the coil 2.

The voltage over A is mains voltage. The time circuit 7 transmits a signal as mentioned above via the conductor 19, i.e. B, according to FIG. 4, slightly, preferably about 2 ms, before the zero-axis crossing of the mains voltage. Hereby the thyristor 21 ignites, whereby the current intensity in the coil 1 follows the curve shown in FIG. 5. During the positive half-cycle of the mains voltage the coil 2 is flown through by current in one direction. After the zero-axis crossing of the mains voltage, the coil 2 is flown through during the negative half-cycle of the mains voltage by current in the same direction as during the positive half-cycle of the mains voltage, due to the diodes 23–26, see FIG. 6.

The double thyristor 21, thus, is of the kind, which at an applied trigger voltage conducts in both directions. Slightly before the zero-axis crossing of the mains voltage, after a full cycle, the time circuit 7 is capable to transmit a negative voltage on the input B, see FIG. 4.

This procedure is repeated at equal time intervals, as indicated in FIGS. 3-6.

The reversing of the current in one or the other of said first coil 1 or said second coil 2 is made to occur within a short time, 1–10 ms, preferably 1 ms, so that two subsequent maxima in the magnetic fields caused by said first coil 1 and said second coil 2 substantially correspond to half a cycle of an alternating voltage with the frequency 50 cps, i.e. 10 ms.

By the device described, thus, is achieved that the coil 1 of the transmitter magnet is flown through by current in two different directions, while the coil 2 of the receiver magnet is flown through by current in one direction during the same time.

The transmission pulse transmitted via the transmitter coil 4 preferably is transmitted about the maximum of the field intensity of the transmitter and receiver magnet. The duration of the transmission pulse is very short, preferably about 10 $\mu$s.

In FIG. 1 the transmitter and receiver are shown as separate units, but they also can be assembled on one frame with a protective casing. From ultrasonic-diagnostic aspects it may be advantageous, that the distance between transmitter and receiver is as short as possible. The closer to one another the units are, the greater are the interferences caused by electromagnet vibrations. This implies that the improvement in the ratio signal-/interference amplitude obtained by the technique described above is very valuable.

The present method, thus, briefly implies that a first transmission pulse is transmitted while the current has the same or different direction in the transmitter and receiver magnets 1,2 and where the signal received is stored in the first memory 8. Thereafter the current in the transmitter magnet 1 or receiver magnet 2 is reversed, whereafter a second transmission pulse is transmitted, whereafter the signal received thereby is stored in the second memory 9.

The signals stored in the memories 8,9 thereafter are subtracted in the difference circuit 10, and the result is transmitted to an analyzer circuit and/or a visual instrument.

It is obvious, that the present invention offers a very simple method and a very simple device for bringing about a substantially improved signal/noise ratio, which is particularly important when the temperature of the test material is high, especially steel above the Curie temperature.

The present invention can be modified in many ways apparent to the expert, without abandoning the idea of the invention. The device for reversing the current in a coil, for example, can be designed by using other known switching elements. During the duration of a strong magnetic field, furthermore, a series of pulses of ultrasonic frequency can be transmitted from the transmitter and receiver magnets, which series is repeated when the polarity has been reversed in one of the transmitter and receiver magnets.

The invention, thus, must not be regarded restricted to the embodiments set forth above, but can be varied within its scope defined by the attached claims.

We claim:

1. An apparatus for non-destructively testing an electrically conductive material, such as steel at a temperature above the Curie temperature, with pulses of ultrasound, comprising first and second core means, a first coil wound on said first core means for producing a first magnetic field in the region of said material upon conduction of electrical current through the first coil, a second coil wound on said second core means for producing a second magnetic field in the region of said material upon conduction of electrical current through the second coil, circuit means electrically connected to one of said first and second coils for conducting current through said one of said first and second coils first in one direction and then in an opposite direction, said circuit means also being electrically connected to the other of said first and second coils for conducting current through said other of said first and second coils, a transmitter coil lying in said first magnetic field, means for conducting a first pulse of current through said transmitter coil to produce at least one ultrasonic pulse in said material while current is being conducted in said one direction through said one of said first and second coils and for further conducting at least a second pulse of current through said transmitter coil to produce at least one additional ultrasonic pulse in said material while current is being conducted in said opposite direction through said one of said first and second coils, a receiver coil lying in said second magnetic field for supplying a first electrical signal in response to said one ultrasonic pulse and a second electrical signal in response to said additional ultrasonic pulse, each of said first and second electrical signals varying as a function of its associated ultrasonic pulse, memory means electrically connected to said receiver coil for storing at least said first electrical signal, an electrical circuit, means for supplying said second electrical signal to said electrical circuit and also for delivering said first electrical signal from said memory means to said electrical circuit, said electrical circuit comprising means for developing an electrical output signal from the difference between said first and second electrical signals to reduce interference in said output signal due to vibration of said first and second coils and said first and second core means, and said output signal containing information for analyzing said material for defects.

2. The apparatus defined in claim 1 wherein said circuit means comprises a pulse generator, said pulse generator comprising a diode rectifier bridge, said other of said first and second coils being connected diagonally across two opposed corners of said bridge, and said one of said first and second coils being connected in parallel with said bridge at the corners of the bridge which are not connected to said other of said first and second coils, said generator further comprising a double thyristor connected to an alternating voltage supply source to apply an alternating voltage across said one said first and second coils and across said bridge such that current conducted through said one of said first and second coils has positive and negative alternations, and said bridge providing for the application of a rectified voltage across said other of said first and second coils such that conduction of current through said other of said first and second coils is unidirectional.

3. A method of non-destructively testing an electrically conductive material, such as steel, at a temperature above the Curie temperature, with pulses of ultrasound, comprising the steps of generating a first magnetic field in the region of said material by conducting a first current through a first coil wound on a core, generating a second magnetic field in the region of said material by conducting a second current through a second coil wound on a core, conducting at least a first pulse of current through a transmitter coil lying in said first field to produce at least one ultrasonic pulse in said material, which, in turn, produces a first electrical signal in a receiver coil lying in said second field, said first pulse of current being conducted through said transmitter coil during a period in which current is passing through one of said first and second coils in one direction and in which current is passing through the other of said first and second coils in a direction which may be the same or opposite to said one direction of current passing through said one of said first and second coils, storing said first electrical signal in a memory, thereafter reversing the direction of current flowing through said one of said first and second coils so that the reverse current passing through said one of said first and second coils is opposite to the direction that it had when said first pulse was conducted through said transmitter coil, and conducting at least a second pulse of current through said transmitter coil while said reverse current is flowing through said one of said first and second coils to produce at least one additional ultrasonic pulse in said material which, in turn, produces a second electrical signal in said receiver coil, and developing an electrical output signal from the difference between said second electrical signal and said first electrical signal in storage to determine the presence or absence of a defect in said material and to reduce interference in the output signal due to vibration of each of the first and second coils and the core on which it is wound.

4. The method defined in claim 3 wherein the flow of said reverse current through said one of said first and second coils is commenced within 1-10 ms following termination of flow of current in said one direction through said one of said first and second coils.

5. The method defined in claim 3 wherein each of said first and second pulses has a preselected pulse width and is conducted through said transmitter coil at a time when the strength of said first magnetic field is at or at least approximately at a maximum.

* * * * *